US00PP10154P

United States Patent [19]

van Andel

[11] Patent Number: Plant 10,154

[45] Date of Patent: Dec. 16, 1997

[54] ALSTROEMERIA PLANT VARIETY NAMED 'STALONA'

[75] Inventor: Jacob van Andel, Aalsmeer, Netherlands

[73] Assignee: Van Staaveren b.v., Aalsmeer, Netherlands

[21] Appl. No.: 629,866

[22] Filed: Apr. 10, 1996

[51] Int. Cl.[6] ..... A01H 5/00

[52] U.S. Cl. ..... Plt./87.1

[58] Field of Search ..... Plt./87.1

*Primary Examiner*—James R. Feyrer

*Attorney, Agent, or Firm*—Christie, Parker & Hale, LLP

[57] ABSTRACT

A new and distinct Alstroemeria plant variety producing flowers of good quality and attractive coloration.

1 Drawing Sheet

BACKGROUND OF THE INVENTION

The present invention relates to a new and distinct variety of Alstroemeria originated as a seedling by crossing as seed parent an unreleased, unpatented seedling identified as 86T1119-01 and as pollen parent an unreleased, unpatented seedling identified as 87G1069-02 from among my collection of Alstroemeria seedlings maintained under controlled conditions in a greenhouse at Van Staaveren B.V., Aalsmeer, The Netherlands, for developmental purposes. The varietal denomination of the new variety is 'Stalona'.

The first act of asexual reproduction of 'Stalona' was in Aalsmeer, The Netherlands, by propagation by dividing rootstocks. Asexual reproduction through successive generations has demonstrated that the combination of characteristics as herein disclosed for 'Stalona' are firmly fixed and retained through successive generations of asexual reproduction.

'Stalona' has not been observed under all possible environmental conditions. Phenotypic expression may vary with variations in environment such as temperature, light intensity, day length and growing and cultural conditions.

SUMMARY OF THE INVENTION

Flowers of the new variety of Alstroemeria, 'Stalona' are characterized by flowers of unusual coloration, as described herein. The plant blooms profusely annually, including production of flower stems in spring and fall under greenhouse conditions in The Netherlands, which is a desirable characteristic in a cut flower variety. The flower-bearing stems are of excellent quality. 'Stalona' grows productively under greenhouse conditions and is also reproducible both by division of rhizomes and by tissue culture.

DESCRIPTION OF ILLUSTRATIONS

The new variety of Alstroemeria hybrid is illustrated in the accompanying illustrations, which shows typical flower characteristics, with colors being as nearly true as is possible for illustrations of this type.

DETAILED DESCRIPTION OF THE NEW VARIETY

The following is a detailed description of the new cultivar of Alstroemeria hybrid as observed in a greenhouse in Aalsmeer, The Netherlands. Color designations indicated are in accordance with The Royal Horticultural Society Colour Chart by color plate designations.

Botanical classification:
- *Family.*—Amaryllidaceae.
- *Genus.*—Alstroemeria sp.
- *Commercial.*—Alstroemeria hybrid.

Origin: Seedling.

Plant

Form: Bush.
Shape: Upright.
Height: About 130 to 160 cm.
Growth rate: Medium.
Main stem or cane length: About 150 cm.
Growth: Vigorous.
Strength: Strong.
Foliage:
- *Quantity.*—Abundant.
- *Number of leaves.*—About 25 to 30 per stem.
- *Size of leaf.*—Length: About 16 to 22 cm. Width: About 3 to 4 cm.
- *Shape of leaf.*—Elliptical.
- *Margin type.*—Straight.
- *Texture.*—Glossy.
- *Color.*—Upper side: Near 137A. Underside: Near 137C.
- *Rhizomes.*—Yes. Color: Near 155D. Size: About 10–30 cm.

Inflorescence — Flower

Blooming habit: Recurrent.
Blooms: Profusely.
- *Spring.*—Yes.
- *Fall.*—Yes.
- *Has tendency to give few blooms in fall.*—No.

Size: Medium.
- *Diameter.*—About 4 to 5 cm.
- *Depth.*—About 5 cm.

Borne: Progressively, along simple racemes.
Shape or form:
- *When bloom first opens.*—Funnel form.
- *When bloom matures.*—Funnel form.

Production: Good annual production, including production of flower stems in spring and fall under greenhouse conditions in The Netherlands.
Petalage:
- *Number of petals.*—6.
- *Arrangement.*—Two concentric circles of 3 petals.
- *Form.*—Obovate.
- *Margin type.*—Minutely crimped.

*Apex.*—Pointed cusped with finely pointed, white protuberances.

*How long do petals stay on stem?*—About 3 weeks.

*Texture.*—Soft.

*Appearance.*—Velvety.

*Color (summer/fall).*—Outer petal/floret: Body near 48B; base near 155D; reverse side near 43C; no stripes each of the outer petals has a distinct central spot near 46A below adjacent the apex. Inside lateral petal: Apical, marginal portions are red, near 43A which changes abruptly, as if in brush strokes, to bright yellow, near 12A. The bright yellow, which is predominant in the central portion of these petals, bleeds gradually to near 43D toward the claw of each inside lateral petal. The color patterns and shadings of the reverse sides follow those of the top surface. Each inside lateral petal contains about 20 to 30 elongated stripes, near 187A, essentially isolated within the bright yellow 12A to 43D portions of the petals. Inside median petal: Body near 43B; base near 43D; reverse side near 43C; 8 to 12 stripes, near 187A.

Peduncle or flower stem:

*Length.*—About 3 to 12 cm.

*Color.*—Near 137B to 137C.

*Strength.*—Strong.

*Upright.*—Yes.

Discoloration after full bloom? Slightly.

Is bloom affected by wet or hot weather? No.

Persistence (does flower hang on and dry?): No.

Disease resistance: Unknown.

Fragrance: None.

Lasting quality:

*On plant.*—About 3 weeks.

*As cut flower.*—About 14 days.

Bud

Size:

*Diameter.*—About 1 to 2 cm.

*Depth or length.*—About 2 to 3 cm.

Form or shape: Pear-shaped.

*Long.*—2 to 3 cm.

*Pointed.*—No.

Rate of opening: Fast.

Color of petals/florets:

*When petals begin to unfurl.*—Near 43A.

Reproductive Organs

Stamen:

*Number.*—6.

*Arrangement.*—Around the style.

Anthers:

*Size.*—About 3 to 4 mm.

*Color.*—Near 4C.

Filaments:

*Length.*—About 2 to 3 cm.

*Color.*—Near 65D.

Pollen:

*Color.*—Copious in quantity and off white to golden, near 20B, in coloration.

Pistils:

*Number.*—1.

Styles:

*Length.*—About 4 to 5 cm.

*Color.*—Near 43A to 43B.

Stigmas:

*Color.*—Near 43C.

Fruit

Fertile: Yes.

Shape: Round.

Color at maturity: Near 163A.

I claim:

1. A new variety of Alstroemeria plant, substantially as herein shown and described.

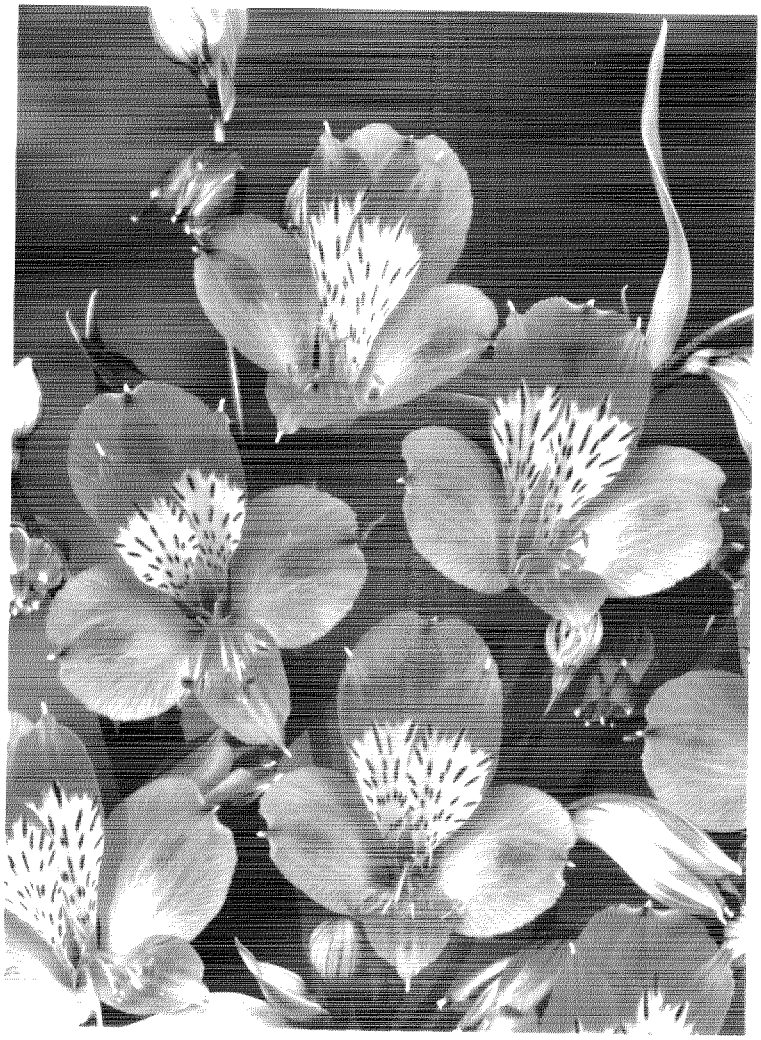

* * * * *